United States Patent [19]

Schrämmli

[11] Patent Number: 5,426,508
[45] Date of Patent: Jun. 20, 1995

[54] MANUAL DENSITOMETER WITH MANULLY OPERATED DIAL

[75] Inventor: Fortunat Schrämmli, Hausen, Switzerland

[73] Assignee: Gretag Aktiengesellschaft, Regensdorf, Switzerland

[21] Appl. No.: 178,381

[22] Filed: Dec. 22, 1993

[30] Foreign Application Priority Data

Dec. 23, 1992 [EP] European Pat. Off. ............ 92811019

[51] Int. Cl.⁶ .............................................. G01J 3/50
[52] U.S. Cl. .................................................. 356/402
[58] Field of Search ............... 356/402, 416, 418, 419, 356/326, 328; 364/498, 526; 250/226

[56] References Cited

U.S. PATENT DOCUMENTS

| | | | |
|---|---|---|---|
| 3,846,027 | 11/1974 | Hyman et al. | |
| 4,870,671 | 9/1989 | Hershyn | 378/124 |
| 4,929,084 | 5/1990 | Mast et al. | 356/446 |
| 4,947,315 | 8/1990 | Sokolow et al. | 395/700 |
| 4,961,646 | 10/1990 | Schrammli et al. | 356/328 |
| 4,968,140 | 11/1990 | Berner | 356/244 |
| 5,319,437 | 6/1994 | Van Aken et al. | 356/328 |

FOREIGN PATENT DOCUMENTS

4027805A1 3/1992 Germany.

OTHER PUBLICATIONS

European Search Report EP 92 81 1019.
Bernina 1530 ® Inspiration (2 pages).
Derwent Database Abstract citing Soviet Union Document 780,068 (1 page).

*Primary Examiner*—F. L. Evans
*Attorney, Agent, or Firm*—Burns, Doane, Swecker & Mathis

[57] ABSTRACT

A manual densitometer for measuring the color composition of an original has a housing which includes a unit for measuring the original, a unit for controlling the measuring, as well as an evaluating electronics and display unit which displays selected variables and parameters. In addition, it has a control unit with a manually-operated dial, which can be rotated from outside the housing, whereby the measuring, the measurement variables, and the parameters for the measurement can be selected by rotating the dial.

14 Claims, 5 Drawing Sheets

MANUAL DENSITOMETER WITH MANULLY OPERATED DIAL

BACKGROUND OF THE INVENTION

The present invention relates generally to a manual densitometer for measurement of the color composition of an original.

Manual meters are generally known, for example such as those in DE-A-40 27 805. This particular device, which is a device for measuring electrical values, can be adjusted to the respective measuring range by a flat disk that is moved manually. Indentations are also provided along the sides of the disk in order to facilitate operation of the flat disk.

In particular, manual densitometers today are widely used aids for measuring the color composition of an original. Such manual densitometers and the special parts of such manual densitometers are known, for example, from U.S. Pat. No. 3,846,027; from U.S. Pat. No. 4,968,140; from U.S. Pat. No. 4,961,646; or from U.S. Pat. No. 4,929,084. Such manual densitometers include a unit for measuring the original; the densitometers of the type disclosed in the patent specifications cited above have a measuring head, which can be extended out of its housing into a measuring position, whereupon it measures the color composition of the original either at a particular point or across a larger area. For example, the color density of the original can be measured for a certain color at a particular point or across a larger area. Selectable measurement variables (for example, the density) as well as specific parameters (for example, the special color whose density is measured) are depicted on a display unit; that is, they are visible to the user on a graphic display, for example with a menu of options on a small monitor, and they can be selected from the displayed menu by means of pushing the corresponding buttons, or other menus, such as sub-menus of the general menu, can be called up by pushing the correct buttons. In turn, once the variables and parameters to be measured have been selected, then the measurement process can be activated by pressing the appropriate buttons so that the measured values appear on the display after the measurement has taken place.

The manual densitometers described above are devices that function well, but there still is room for improvement. For example, activating the keyboard buttons for controlling the measurement process has the disadvantage that the speed with which the menus are run through by pressing the keyboard buttons (running up and dow the menu) is always tied to the same fixed reaction time at which the pressing of a button is convened into the corresponding change on the display unit. The user has no influence on this reaction time, namely the user cannot decrease this amount of time.

In addition, such a keyboard of buttons also has the disadvantage of being relatively bulky and of being difficult to operate by hand. In the case of such manual densitometers, it has to be noted that a user usually has to hold with one hand the original being measured, whereas the other hand is used to hold and operate the manual densitometer. This usually means, however, that whenever the user has to hold the densitometer in his hand, then he can only move his hand slightly. If the keyboard of buttons is relatively large, then it is all the more difficult to operate. Furthermore, the keyboard requires a relatively large amount of space, which is a rare commodity in hand-held devices.

User-friendly graphics are also well known in the computer field. In particular, the well-known mouse has proven to be particularly suitable as a pointer and control instrument. But because of the space problems mentioned above, it is not practical for hand-held equipment. The mouse operates with a two-dimensional "trackball", which converts the motion of the rotary ball into a corresponding movement of the mouse's pointer. This trackball, which is clearly superior to a keyboard for saving space, is already being used on its own as a select and control instrument in other devices for selecting certain parameters or functions. For example, such a trackball is used for selecting certain types of stitches in a sewing machine under the model name of "BERNINA 1530 ® Inspiration." But this sewing machine always has to be firmly positioned on a flat surface so that the user can easily move his hand in order to operate the trackball. But even then, this kind of trackball still has the disadvantage that the selected parameters can change easily with the slightest movement of the trackball, because a change in the position of the trackball, regardless of what direction it is, results in a corresponding change in the position of the pointer in the menu. As a result, the selection of individual options or parameters in the menu becomes more difficult because the precise command to call up the desired option or the desired parameters in the menu is made comparatively more difficult with the trackball.

SUMMARY OF THE INVENTION

In light of the above, one of the purposes of the invention is to eliminate the afore-mentioned disadvantages and to make available a manual densitometer with a select and control instrument, which is also easy to operate and allows for a reliable selection of measurement functions, parameters or, for example, of individual options from a menu if the user only has one hand available for holding and for operating the densitometer.

In accordance with the invention, this task is solved by the fact that the control unit of the manual densitometer includes a manually-operated dial (e.g., circular dial) that can be rotated outside of its housing, whereby measurement functions, variables to be measured as well as the parameters for the measurements can be selected by turning the circular dial. This kind of manually-operated circular dial has a number of advantages. On the one hand, the chance that the measurement function, the selected parameter or the selector variable would change is limited to only "one" dimension—the dial can only be rotated on "one" plane around a stationary axis—so that the setting of the desired measurement function, of the desired parameter, or of the desired variable is made considerably easier than with a trackball. This makes it significantly easier to operate the densitometer, especially if the user has to hold and operate the densitometer in the same hand so that under extreme conditions he has only one finger to operate the densitometer. Even under such extreme conditions, it is possible to comfortably use the densitometer proposed by the invention.

One exemplary embodiment of a manual densitometer of the proposed invention includes a stator with a hollow, cylindrical stator body. The stator body is positioned around a longitudinal axis of the manually-operated circular dial in an axially symmetrical fashion.

A magnetic catch, in this instance, is designed in such a way that the stator body has alternating magnetic poles along its periphery at equal intervals. The circular dial has an essentially hollow cylindrical rotor tube, which is positioned coaxially to the stator body and surrounds it. On its interior wall, the rotor tube has cogs that face the stator body; these cogs are spaced at the same interval as that of the magnetic poles on the periphery of the stator body. Whenever a magnetic pole of the stator body is brought into a rest position against a cog of the rotor tube, then a stable fixed position is established. This embodiment is distinguished by its simple design and by its simple and cost-effective way to produce the individual pans. In addition, unstable "in-between" positions of the circular dial are prevented by this design.

Another exemplary embodiment of a manual densitometer proposed by the present invention includes two disks, which are positioned parallel to each other and are positioned on a plane that is vertical with respect to the longitudinal axis of the circular dial (that is axially symmetrical around its axis). The two stator disks are connected to each other by a circular magnet, the magnetic field of which runs essentially in the direction of the longitudinal axis of the circular dial. The magnetic catch in this embodiment is designed in such a way that the manually-operated circular dial includes an essentially hollow, cylindrical rotor tube that is positioned coaxially to the stator disks and surrounds them, and the stator disks have an outward-oriented gear tooth system. On its interior wall, the rotor tube is also cogged with cog intervals that are the same as those of the stator disks (i.e., cogs on the interior wall of the stator disk). So, whenever the cogs of the gear wheel on the interior wall of the rotor tube come to rest against the outward-oriented gear teeth of the stators, then the air gap between the rotor tube and the stator is at a minimum and the magnetic field is closed—this position, then, corresponds to that of a stable, fixed position. This embodiment is distinguished by the fact that it is easy to implement. In addition, unstable "in-between" positions are, of course, also prevented in this embodiment.

The manual densitometer of the present invention can be further configured so that the stator disks or the magnetized stator are firmly secured to a bearing sleeve and that the rotor tube is equipped with a central shaft that can rotate within the beating sleeve and can be rotated together with the rotor tube with respect to the bearing sleeve. This central shaft is connected to a detection unit, which detects a given position and a direction of rotation of the rotor tube to generate a corresponding signal and to guide it to the evaluating electronics. In this embodiment, the position of the rotor tube can be detected with the aid of the detection unit and its position can be converted into a corresponding electrical signal so that, for example, a menu can be run through in simple fashion only by the user turning the rotor tube in the desired direction.

The detection unit can have two stationary fight barriers and a cogged disk that is connected to the central shaft of the rotor tube. The cogged disk is positioned between the light source and receiver of the light barrier. The two fight barriers themselves are positioned relative to each other so that the signal generated by the one light barrier is phase-shifted to the signal generated by the other light barrier. In particular, the light barriers are positioned relative to each other in such a way that the signals generated by the individual light barriers are, for example, phase-shifted by 90° with respect to each other. With the aid of the two phase-shifted signals, it is possible to determine in a simple way the direction in which the manually-operated circular dial is being turned, depending upon which signal precedes or succeeds the other.

The light barriers can be implemented, for example, in such a way that the light source is designed as a light emitting diode and the receptor as a photodiode. A slit diaphragm is located between the light emitting diode and the photodiode; the slit of the slit diaphragm is narrow with respect to the width of a cog of the cogged disk, which is connected to the rotor tube. As a result, one achieves, on the one hand, steep upward and downward slopes for each generated signal that can be easily detected. The result is that the position of the rotor tube can be detected precisely and can be converted into a display via a corresponding selection of the display unit. On the other hand, any possible outside light entering at an angle cannot be recognized by the detector as a light signal from the assigned light emitting diode because it is virtually screened by the slit diaphragm.

Another exemplary embodiment of a manual densitometer of the present invention is distinguished by a control unit which includes an electronic turn off/turn on switch that switches the power supply from the operating mode into a stand-by mode, at least for some components of the manual densitometer, after a defined interval of time has passed in which no change in a functional state of the manual densitometer has occurred. This aspect of the invention is very significant, as is shown in the following comments. Usually, manually-operated devices are battery-powered or are equipped with rechargeable power packs, and the energy needs of such a device, if used on a constant basis, are relatively high (especially the power consumption of the light barriers). As a result, a device in accordance with the present invention can be operated for longer periods of time than if it had been operated constantly with the batteries or rechargeable power packs making available a constant power supply. On the other hand, the device is, of course, supposed to be fully ready to use at any time the user wants to operate it. For this purpose, a turn on switch can be made available for immediately switching the energy supply into the operating mode once a change in the functional state has occurred in the manual densitometer.

This turn on switch can be in the form of a coil that is positioned coaxially to a circular magnet; once the magnetic flow that goes through the coil has changed, then a corresponding signal is generated and is guided to the electronic turn off/turn on switch. This solution is distinguished by a low level of complexity, but (on the other hand) has a lower response time. Depending upon the desired sensitivity, the energy supply can be switched rapidly and reliably to the operating mode by slightly changing the magnetic flow through the coil.

BRIEF DESCRIPTION OF THE DRAWINGS

Other objects and advantages will become apparent from the following detailed description of preferred embodiments of the invention as described in conjunction with the accompanying drawings wherein like reference numerals are applied to like elements and wherein.

DETAILED DESCRIPTION OF THE PREFERRED EMBODIMENTS

Figure 1:
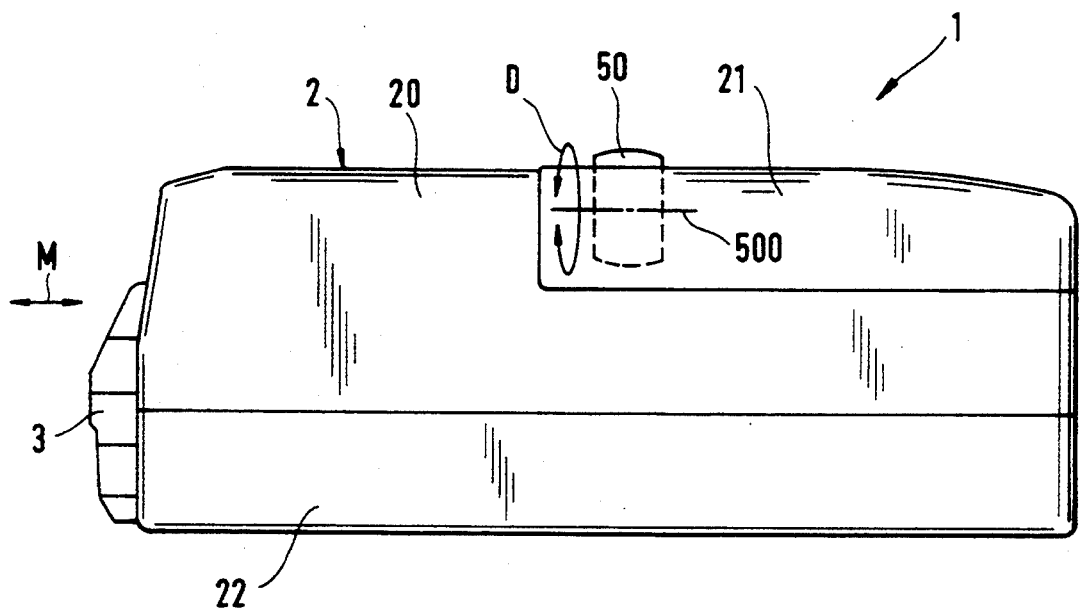
FIG. 1 shows an exemplary embodiment of a manual densitometer in accordance with the invention in a side view.
Figure 2:
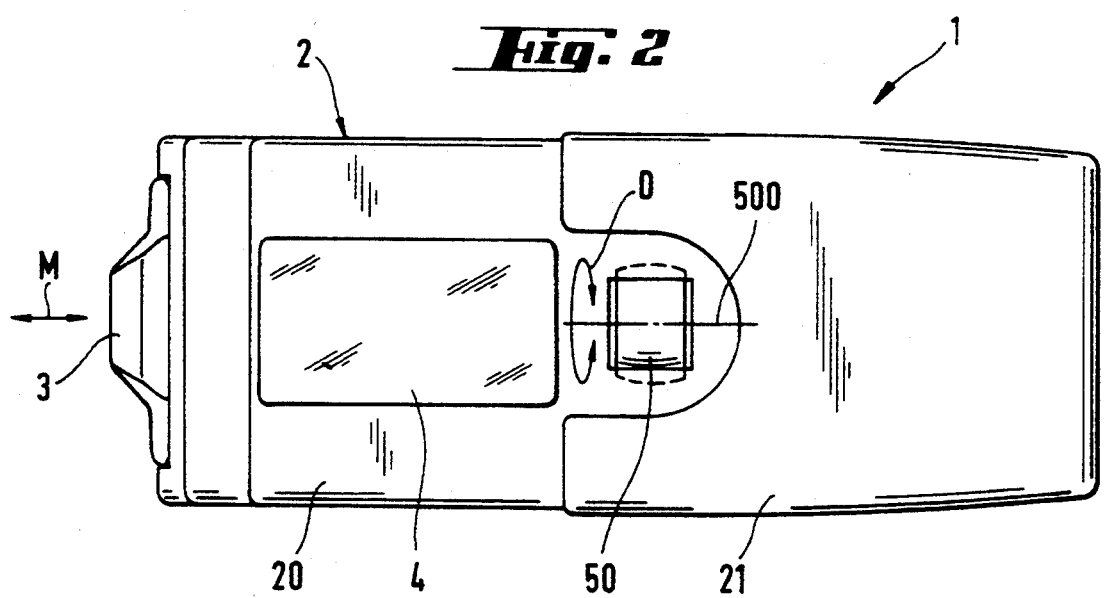
FIG. 2 shows an exemplary embodiment of the manual densitometer according to FIG. 1 in a top view.

An exemplary embodiment of a manual densitometer 1 in accordance with the invention is depicted in FIGS. 1 and 2. It includes a housing 2 with numerous housing components 20, 21 and 22, and a measurement device, the measuring head 3 of which can be seen. The measuring head 3 can be extended out of the housing 2 in the direction of arrow M for conducting measurements, and can then be reinserted into its rest position, as is shown in FIGS. 1 and 2. Furthermore, the manual densitometer 1 also has a display unit 4 as well as a manually-operated dial (e.g., circular dial) 50, that can be rotated in the direction of arrow D. The function of the circular dial 50 in conjunction with the display unit 4 is described in greater detail below.

Figure 3:
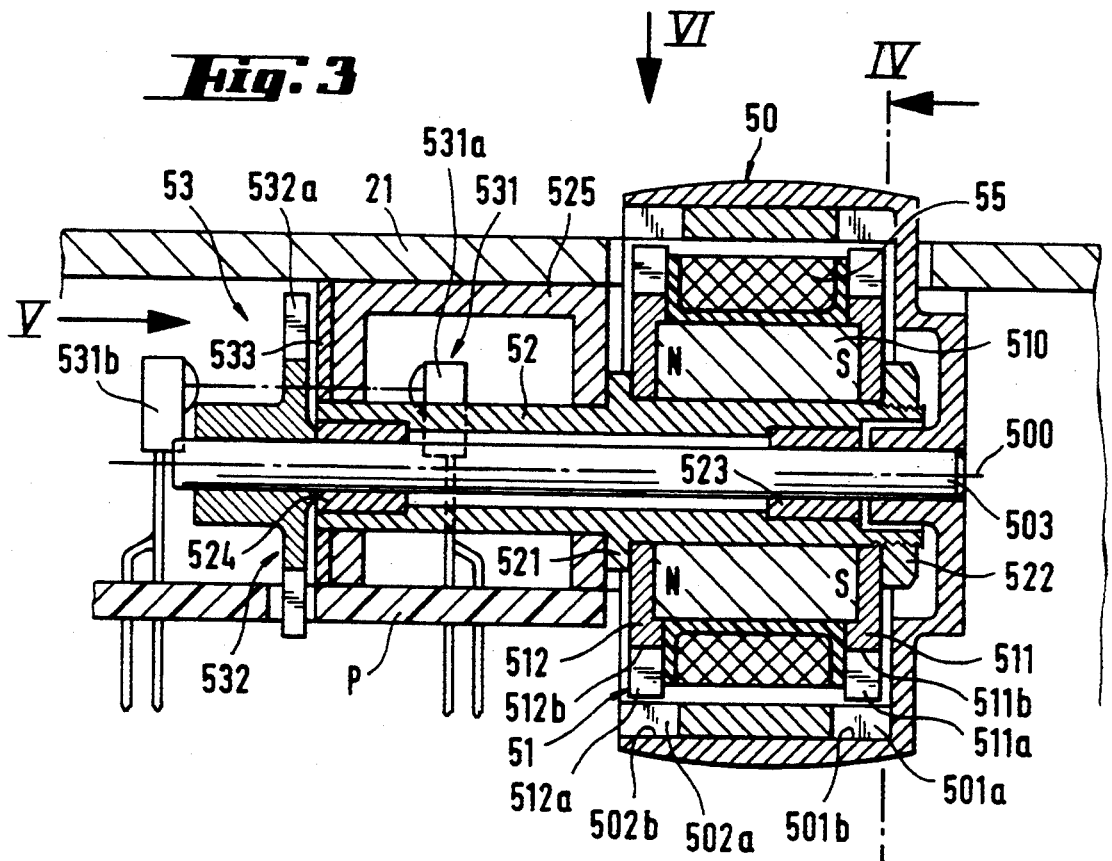
FIG. 3 shows an exemplary embodiment of the magnetic catch of a manual densitometer in accordance with the invention.

In FIG. 3, the circular dial 50 that has already been mentioned in the explanation of FIGS. 1 and 2 can be recognized again. The circular dial 50 is designed as a hollow, cylindrical rotor tube that coaxially surrounds a stator 51. The stator 51 has two stator disks 511 and 512 as well as a tube-like or ring-like magnet 510. The two stator disks 511 and 512 are positioned parallel to each other and each extends vertically with respect to the longitudinal axis 500 of the circular dial 50. The magnetic field of the magnet 510 essentially ranges in the direction of the longitudinal axis 500 of the manually-operated circular disk.

As an example of an magnetic field, FIG. 3 illustrates a magnetic north pole N indicated at the one end and a magnetic south pole S indicated at the other end. Both the two stator disks 511 and 512 as well as the circular magnet 510 are fixed to a bearing sleeve 52 which is axially symmetrical, that is positioned coaxially with respect to the longitudinal axis 500 of the circular dial (rotor tube) 50. As a result, the stator disks 511 and 512 as well as the circular magnet 510 are positioned coaxially to the longitudinal axis. The stator disks and the magnets can, for example, be fixed with the aid of a stop 521 on the bearing sleeve 52 and held in position by a nut 522. The circular dial 50 is equipped with a central shaft 503, which is positioned within the bearing sleeve 52 and, as a result, provides an ability of the circular dial 50 to rotate relative to the entire stator 51.

Figure 4:
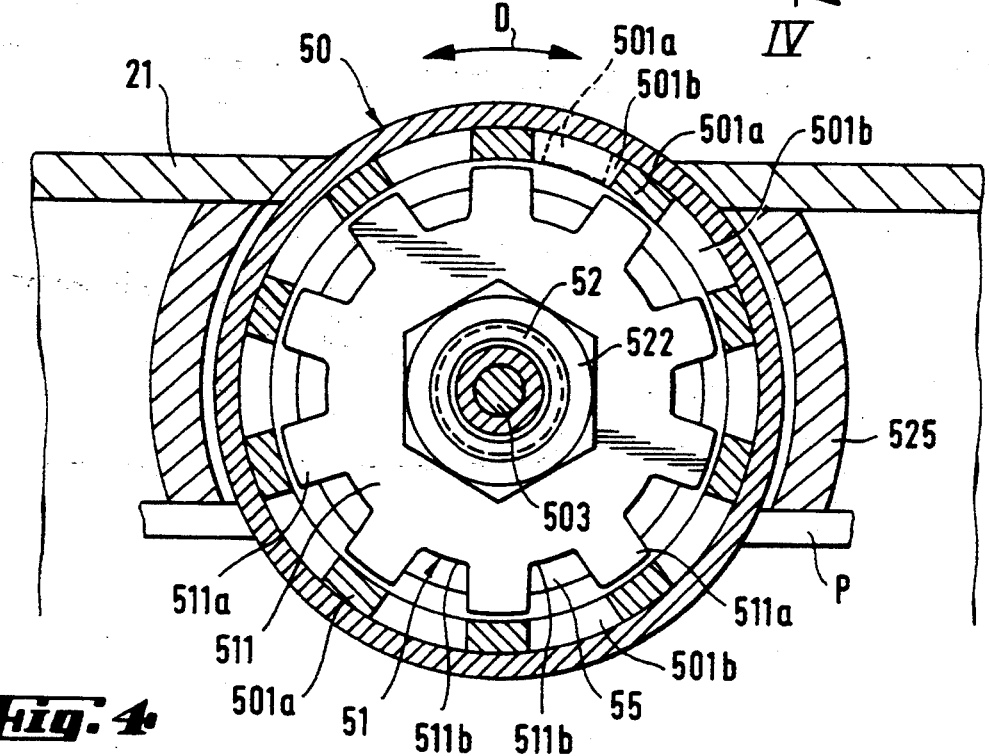
FIG. 4 shows a sectional view along line IV—IV of FIG. 3.

The two stator disks 511 and 512 are equipped with outward-oriented cogs; the individual cogs 511a and 512a and the corresponding intervening spaces 511b and 512b have equally spaced intervals from each other and provide for regular spacing. On its interior wall, the rotor tube 50 has two corresponding cogged wheels, which in turn have individual cogs 501a and 502a as well as intervening spaces 501b and 502b which are also regularly spaced. The cogged wheels on the interior wall of the rotor tube 50 are coaxial to the cogs of the stator disks 511 and 512. The spacing of the cogs on the stator disks 511 and 512 and the spacing of the cogs on the interior wall of the rotor tube, 50 are the same. This can be seen especially well in FIG. 4 in which a section along lines IV—IV of FIG. 3 is illustrated. In this figure, the cogs 511a of the stator disk 511 are set directly opposite the cogs 501a of the gear teeth on the interior wall of the rotor tube 50. As a result, the air gap between these cogs is at a minimum and the magnetic field is closed by the two cogs as well as by the cogs 502a of the rotor tube 50 and cogs 512a of the other stator disk 512 and finally by the circular magnets which connect the two stator disks 511 and 512. In this way, a magnetic catch is made possible in which the circular dial 50 as shown in FIG. 4, is found in the stable fixed position. If the circular dial is located in a position in which the cogs of the gear teeth are not positioned opposite each other (in FIG. 4, one cog is indicated by dotted lines in such a position), then the magnetic field is not closed, and torque is applied to the circular dial, moving it into the stable fixed position.

Figure 5:
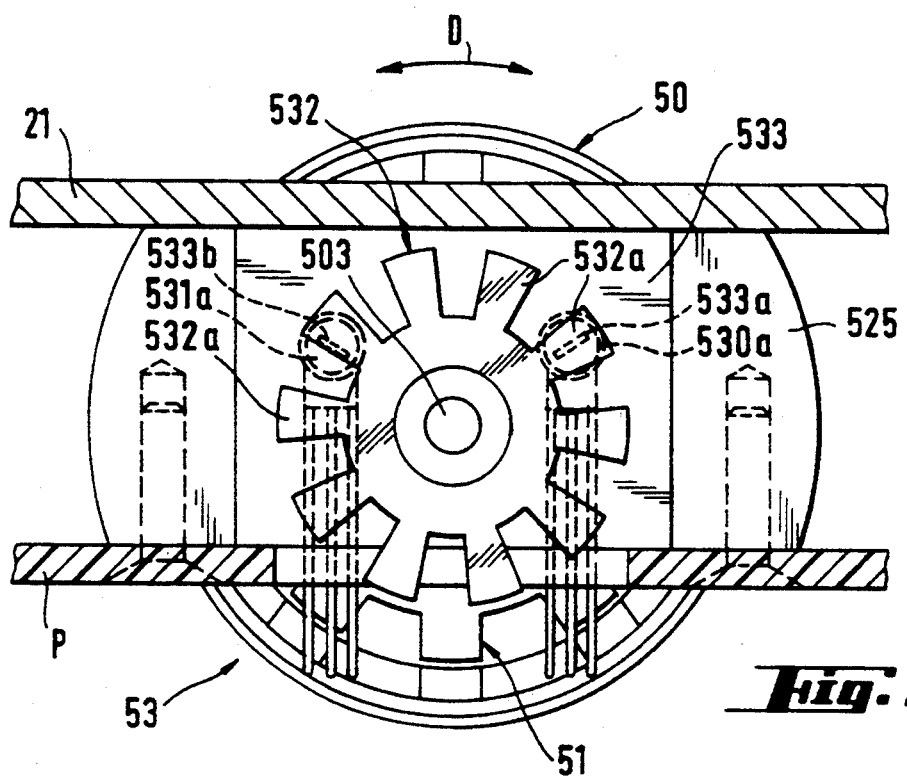
FIG. 5 shows a view according to arrow V of FIG. 3.

A detection unit 53 is connected to the shaft 503 of the circular dial 50. This detection unit is visible in FIG. 3, in FIG. 5, and in FIG. 6. It detects the position and the direction of rotation of the rotor tube 50 at any given time and it sends a corresponding signal to an evaluating electronics, which is described in greater detail below. The detection unit 53 has two stationary fight barriers 530 and 531, each of which in an exemplary embodiment has as a light source a light diode 530a and 531a respectively, located in a screen 525 to protect against outside light, as well as a photodiode 530b and 531b, respectively, as a receiver. Connecting wires of these dimes are connected to a circuit board P (FIG. 3). A cogged disk 532 is located between the light barriers 530 and 531; in this embodiment, the spacing between the cogs of this disk is the same as the spacing of the cogs on the stator disks or of the rotor tube (FIG. 5). Furthermore, a slit diaphragm 533 is also positioned between the light barriers; slits 533a and 533b of the slit diaphragm are very narrow in comparison with the width of a cog on the cogged disk 532. The slit diaphragm 533 is firmly connected to the screen 525.

Figure 6:
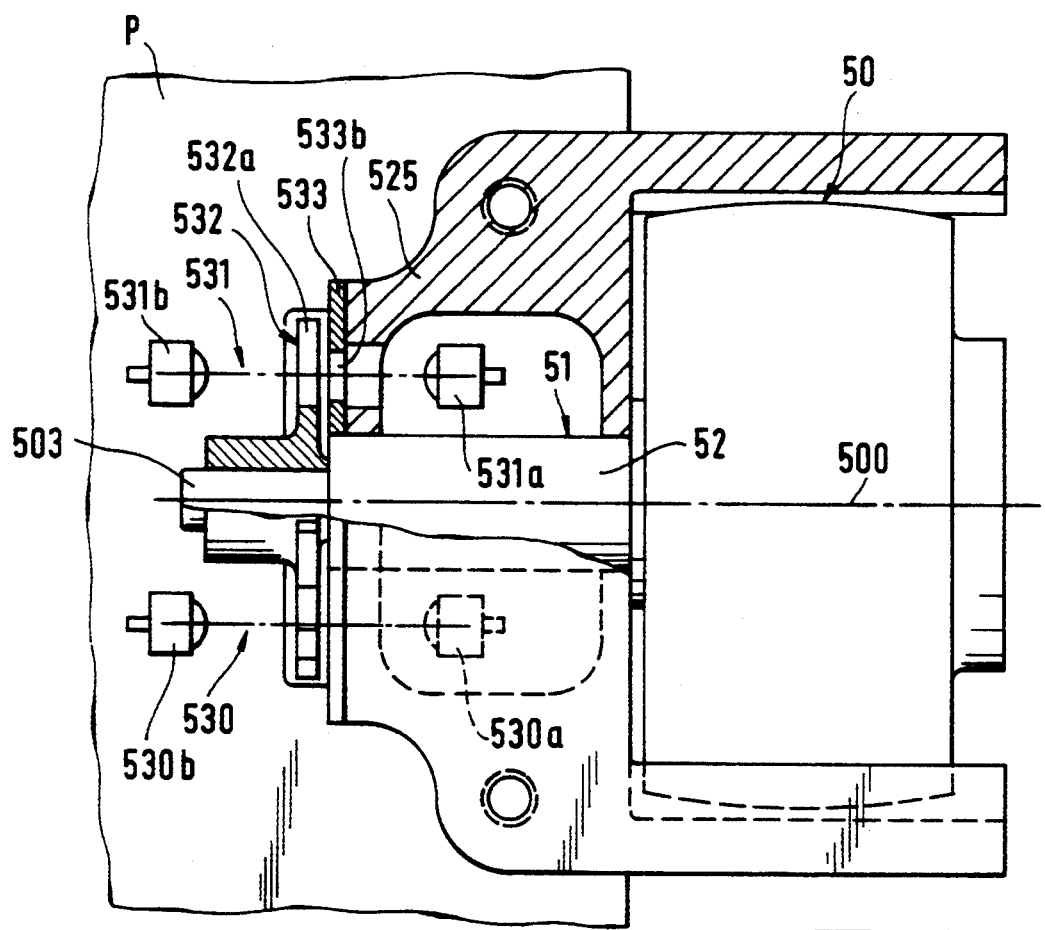
FIG. 6 shows a top view according to arrow VI of FIG. 3.

The way the detection unit 53 operates can be explained with the aid of FIGS. 5 and 6. It should be noted that in an exemplary embodiment the circular dial is rotated in a clockwise direction. The cogged disk 532 in the position shown here, is about to let the light of the light emitting diode 531a (FIG. 6) enter through the slit 533b, so that it immerses the concomitant photodiode 531b (FIG. 6), which then generates a corresponding electrical signal. Because of the narrow slit 533b the signal has a corresponding steeply sloped upward curve (a downward curve for an inverted signal). As a result, the time at which the signal appears is detected precisely by electronic means. The slit 533a on the other hand is covered in the illustrated position of the cogged disk 532 by a cog 532a of the disk 532, so that the light from the light dime 530a (FIG. 6) cannot expose the concomitant photodiode 530b (FIG. 6).

If the circular dial is rotated further in a clockwise direction, then the photodiode 530b also detects an upward sloped signal a short time after the photodiode 531b has detected the upward sloped signal. Specifically, this occurs when the cog 532a, which still prevents the penetration of light to the photodiode 530b in the illustrated position of the disk 532 releases the passage of light to the photodiode 530. In the embodiment shown here, the light barriers 530 and 531 are positioned in such a way that the signals are phase-shifted by 90°. This shifted phase is very easy to detect. Given the illustrated embodiment of the detection unit 53 it is particularly easy to determine the speed at which the circular dial is rotated with the aid of the number of sloped signals detected over a certain period of time. It is also possible in a similarly easy way to determine the rotational direction of the manually-operated circular dial with the aid of the shifted phase of the signals generated by the light barriers because it is simply determined which signal precedes the other, in this instance at an angle of 90°.

Figure 7:
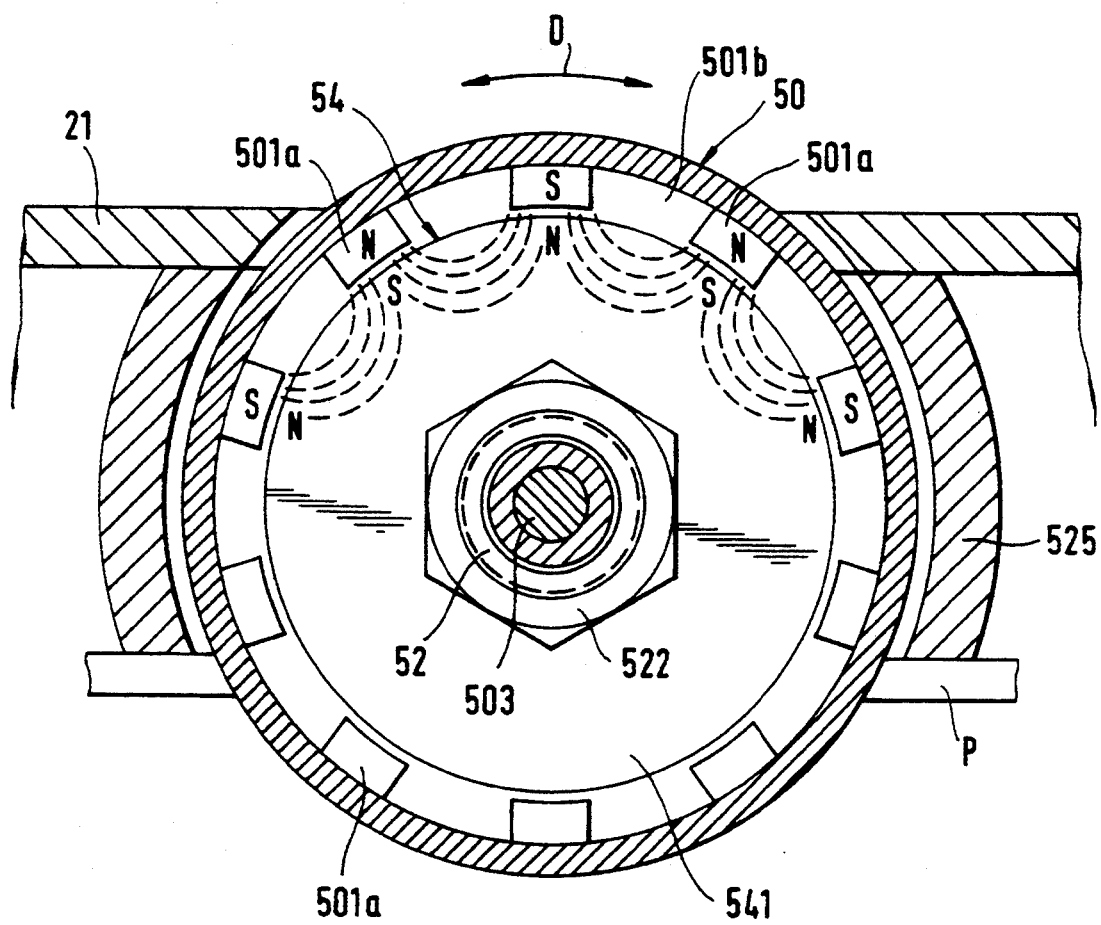
FIG. 7 shows another exemplary embodiment of a magnetic catch of a manual densitometer in accordance with the invention.

Another exemplary embodiment of a magnetic catch is illustrated in FIG. 7. In principle, this depiction is the same as the one in FIG. 4 except that the stator 54 is designed differently than the stator 51 shown in FIG. 4. The stator 54 illustrated in FIG. 7 has a laterally magnetized stator body 541 which is magnetized in such a way that the magnetization has alternating magnetic poles—magnetic north poles N and magnetic sought poles S—at equal intervals along the periphery of the stator body. The spacing of the alternating magnetic poles N and S corresponds to the spacing of the cogs on the interior wall of the rotor tube 50. The magnetic field extends from one of the poles of the stator body 541 through the cog located on the opposite side of this pole on the interior wall of the rotor tube 50 and runs further through the rotor tube 50 to the neighboring cog, and again back through the neighboring cog to the stator body 541. The magnetic field is closed once a pole of the stator body 541 is positioned opposite a cog located on the interior wall of the rotor tube. The rotor tube 50 is then in a stable fixed position. Otherwise, torque is applied to the rotor tube 50 moving it into a fixed position similar to the embodiment explained with the aid of FIG. 4. If the rotor tube or the circular dial 50 is moved out of a fixed position into the next fixed position, then the distribution of the poles on the cogged wheel (the north and south poles) also "change," because in the next fixed position the same cog that previously was opposite a magnetic north pole is now positioned opposite a south pole.

At this point, another significant aspect of the invention should be discussed, and it can be used in both exemplary embodiments described above, but for reasons of simplicity it is illustrated only for the first embodiment that has been described. This relates to the coil 55 (FIG. 3) that is positioned around the circular magnet 510. As soon as the manually-operated circular dial or the rotor tube 50 is rotated, then the magnetic flow through the coil 55 is changed and it induces an electrical current. This induced current is fed to an electronic turn on/turn off switch, which will be described in further detail below with the aid of FIG. 8. With the aid of the coil 55 and the turn off/turn on switch described below, the apparatus can be switched out of the operating mode into a stand-by mode after a defined time interval has passed in which there has been no change in the operating parameters of the device. But as soon as the circular dial is moved, the magnetic flow through the coil 55 changes, a current is induced in it, and, as a result, the apparatus is again immediately switched into the operating mode by means of the turn off/turn on switch. This measure increases the lifespan of the apparatus because the power for such equipment usually is supplied with batteries or rechargeable power packs. On the other hand, the light barriers 530 and 531 alone require so much energy when they are being operated that the energy stored in the batteries or rechargeable power packs would be consumed within a comparatively short period of time. By means of the coil 55 and the turn off/turn on switch, the period of time during which the apparatus is operational can be decreased considerably to increase the lifespan of the apparatus. Simultaneously, the apparatus is immediately operational whenever the device is turned on during this period of time.

Figure 8:
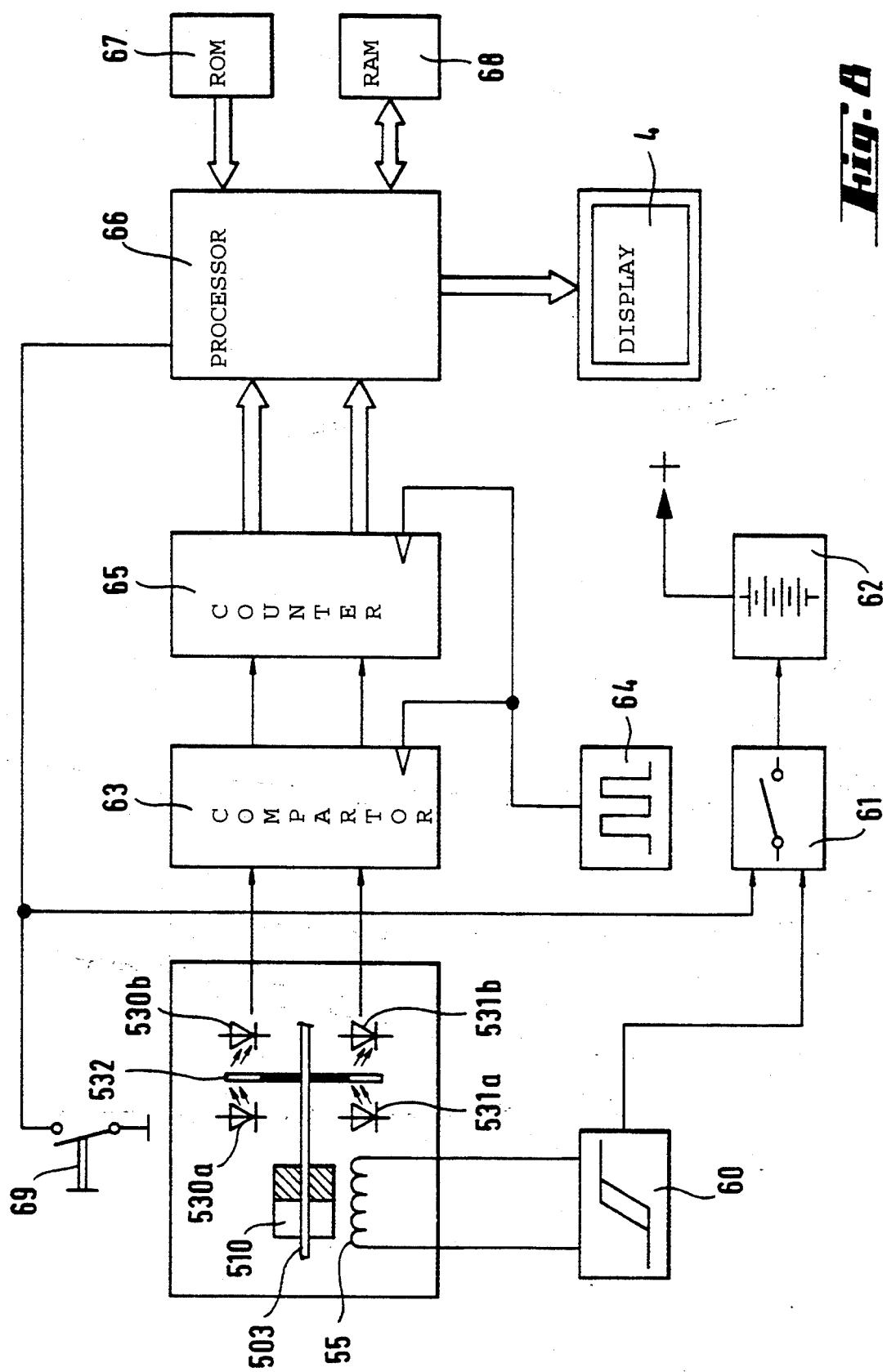
FIG. 8 shows an exemplary embodiment of an electronic turn off/turn on switch and other electronic details of a manual densitometer in accordance with the invention.

An exemplary embodiment of the electronic turn off/turn on switch as well as other electronic details are schematically illustrated in FIG. 8. The turn off/turn on switch has a computing recording comparator 60 as well as an on/off switch 61, which is connected to a power supply 62. The outlet of the power supply 62 is illustrated only symbolically with an "+", which is supposed to indicate that diverse (power) consumers in the apparatus are supplied by this power source. A current, which switches on the comparator 60 is induced in the coil 55 when the magnetic flow through the coil is changed (for example, by rotating the manually-operated circular dial 50). In turn, the turn off/turn on switch 61 is activated, which immediately activates the power supply 62. The two light emitting diodes 530a and 531a as well as the corresponding photodiodes 530b and 531b are indicated in FIG. 8. The output signals of the photodiodes 530b and 531b are connected to a circuit 63, which compares the phase relationship of the signals that are generated by the photodiodes 530b and 531b and depending upon the phase relationship, a counter 65 is incremented or reduced; the cycles for this purpose are produced by an oscillator 64. A processor 66 reads the counter cyclically. Software in a ROM memory 67 stores the actual position of the circular dial on the basis of the counter data. A change in this position is then convened by the processor 66 into a corresponding change in the selected menu line or into an increment or reduction in a value in an adjustable RAM memory 68 and guides a corresponding signal to the display unit 4, which then changes the display correspondingly. In this way it is very simply possible to run through a menu on the display unit 4 by rotating the circular dial 50 or to change the value of a desired parameter, whereby this change is immediately depicted on the display unit 4.

Should a measurement be initiated, then it can be done with the aid of a symbolically depicted button 69. On the one hand, this button 69 is connected to the processor 66 in order to give it the "information" that a measurement is supposed to occur now; on the other hand, it is also connected to the turn off/turn on switch 61. Should the apparatus be in a stand-by position, it has to be switched immediately into the operational position so that the measurement can take place. By means of the button, therefore, individual menu options or parameters can be selected. But this is possible only if the circular dial 50 is found in a stable fixed position, as described in detail above.

A change in the position of the manually-operated circular dial 50 can be detected in a different way as will be described with the exemplary embodiment with the laterally magnetized stator body 541 described with the aid of FIG. 7, whereby the power supply 62 can be switched immediately from the stand-by mode to the operating mode. For this purpose the light barriers 530 and 531 do operate constantly, but only in such a way that they have pulsed emissions; for example, the light barriers can be turned on fifty times a minute for a few microseconds, and then are turned off again. The power consumption of the light barriers is also very low when operated in this stand-by mode. The return to the operating mode can occur by reading the counter 65. If the position of the counter 65 changes—it changes only when the circuit 63 also detects a changed phase relationship of the signals that are emanating from the photodiodes 530b and 531b—then the power supply 62 is again immediately switched to the operating mode. In addition to the very low power consumption, this means of switching to the fight mode is also characterized by the fact that it can react very quickly at a correspondingly high pulse frequency and the apparatus can be switched from the stand-by mode to the operating mode very quickly.

The densitometers of the invention, therefore, provide a number of advantages from many points of view. First, an ability to change the desired parameter or the desired variable is limited to only "one" dimension—the manually-operated circular dial need only be rotated around a stationary axis on "one" plane—so that setting the desired parameter or the desired variables is considerably easier than with a trackball. This simplifies operation of the densitometer considerably, especially if the user has to hold and operate the densitometer with the same hand so that in extreme cases only one finger could be available for operating the densitometer. Even under such extreme conditions, it is also possible to operate a densitometer of the invention comfortably.

In addition, such a densitometer also has other advantages: because the circular dial converts a rotating action quickly into a corresponding signal, a menu on the screen of the display unit can be run through quickly as well. If a number of options have to be skipped in order to arrive at the desired option then the user only has to rotate the circular dial accordingly.

Furthermore, the manually-operated circular dial cannot be positioned in a stable fashion between two options, but rather the catch always moves the circular dial into a fixed position. The fixed position is assigned to a specific option in the menu so that the apparatus is always in a precisely defined mode. Once an option, a parameter, or a variable has been selected in a fixed position, then the dial cannot slip out of position easily. Accordingly, the selected option, the selected parameter, or the selected variable cannot change unintentionally.

With the help of the light barriers, the direction of rotation and the speed of rotation can be detected in simple fashion and can be converted into a corresponding display. The electronic turn off/turn on switch allows for longer operating time of the manual densitometer because such devices usually are equipped with a power supply from a battery or rechargeable power pack.

It will be appreciated by those skilled in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description and all changes which come within the meaning and range of equivalents thereof are intended to be embraced therein.

I claim:

1. Manual densitometer for measuring the color composition of an original, comprising:
    a housing which includes a unit for measuring the original, a unit for controlling the measuring, an evaluating electronics and a display unit which displays at least one selected measurement function, variable or parameter; and
    a manually-operated dial operatively connected with said controlling unit, which can be rotated from outside the housing such that selected measurement functions, variables and parameters for the measuring can be selected by rotation of the dial.

2. Manual densitometer in accordance with claim 1, further comprising:
    a magnetic catch for moving the dial into a fixed position if it is not located in a fixed position, and for maintaining the dial in the fixed position.

3. Manual densitometer in accordance with claim 2, wherein said display unit is operatively connected with said dial such that plural menus are made visible on the display unit one menu or an individual option being selectable via the dial if the dial is in a fixed position.

4. Manual densitometer in accordance with claim 2, wherein said magnetic catch further includes:
    a stator with a hollow cylindrical stator body which is placed in axially symmetrical fashion around a longitudinal axis of the dial, the stator body having alternating magnetic poles at equal intervals along its periphery and the dial having an essentially hollow, cylindrical rotor tube located coaxially to and surrounding the stator body, such that the rotor tube has interior cogs that face the stator body and these cogs have a spacing equal to a spacing of the magnetic poles on the periphery of the stator body.

5. Manual densitometer in accordance with claim 2, wherein said magnetic catch further includes:
    two stator disks that are parallel to each other and extend vertically relative to a longitudinal axis of the dial in axially symmetrical fashion around the longitudinal axis, the two stator disks being connected to each other by a circular magnet having a magnetic field which essentially runs in a direction of the longitudinal axis of the dial, the dial having an essentially hollow, cylindrical rotor tube coaxial to and surrounding the stator disks, the stator disks each having outward facing cogs and the rotor tube having two sets of cogs on its interior wall, each set of cogs on the interior wall being coaxially arranged to the cogs of the respective stator disk and the cogs of each set of cogs having a spacing between one another which is equal to the spacing of the cogs of the respective stator disk.

6. Manual densitometer in accordance with claim 4, wherein the stator body is positioned on a beating sleeve and the rotor tube has a central shaft that can be rotated in the bearing sleeve for rotation together with the rotor robe in relation to the bearing sleeve, the central shaft being connected to a detection unit which detects a given position and a direction of rotation of the rotor tube and generates a corresponding signal which is directed to the evaluating electronics.

7. Manual densitometer in accordance with claim 5, wherein the two stator disks are positioned on a bearing sleeve and the rotor robe has a central shaft that can be rotated in the beating sleeve for rotation together with the rotor robe in relation to the bearing sleeve, the central shaft being connected to a detection unit which detects a given position and a direction of rotation of the rotor tube and generates a corresponding signal which is directed to the evaluating electronics.

8. Manual densitometer in accordance with claim 6, wherein the detection unit further includes:

two stationary light barriers and a cogged disk connected to the central shaft of the rotor tube and positioned between a light source and a receiver of the light barriers, the light barriers being positioned relative to each other such that the signal generated by one of the light barriers is phase shifted with respect to the signal generated by the other light barrier.

9. Manual densitometer in accordance with claim 7, wherein the detection unit further includes:

two stationary light barriers and a cogged disk connected to the central shaft of the rotor tube and positioned between a light source and a receiver of the light barriers, the light barriers being positioned relative to each other such that the signal generated by one of the light barriers is phase shifted with respect to the signal generated by the other light barrier.

10. Manual densitometer in accordance with claim 8, wherein the light source of each light barrier is a light emitting dime and the receptor of each fight barrier is a photodiode, a slit diaphragm being positioned between the light emitting diode and the photodiode and including slits which are narrow with respect to a width of a cog of the cogged disk connected to the central shaft of the rotor tube.

11. Manual densitometer in accordance with claim 9, wherein the light source of each light barrier is a light emitting diode and the receiver of each light barrier is a photodiode, a slit diaphragm being positioned between the light emitting diode and the photodiode and including slits which are narrow with respect to a width of a cog of the cogged disk connected to the central shaft of the rotor tube.

12. Manual densitometer in accordance with claim 1, wherein the controlling unit further includes:

an electronic turn off/turn on switch for switching a power supply for at least one component of the manual densitometer from an operating mode into a stand-by mode after a defined period of time has passed in which there has been no change in a functional state of the manual densitometer, and a turn on switch that again switches the power supply into the operating mode upon a change in the functional state of the manual densitometer.

13. Manual densitometer in accordance with claim 12, wherein the turn on switch further includes:

a coil that is coaxial to a circular magnet for generating a turn on signal when there is a change in magnetic flow through the coil and for directing the turn on signal to the electronic turn off/turn on switch.

14. Manual densitometer in accordance with claim 1, wherein the dial further includes:

a circular dial for selecting variables to be measured and for selecting parameters for measuring the original via the controlling unit.

* * * * *